(12) United States Patent
Wang

(10) Patent No.: US 10,576,015 B2
(45) Date of Patent: Mar. 3, 2020

(54) PRESSURIZING DEVICE

(71) Applicant: Yu-Chien Wang, Taichung (TW)

(72) Inventor: Yu-Chien Wang, Taichung (TW)

(*) Notice: Subject to any disclaimer, the term of this patent is extended or adjusted under 35 U.S.C. 154(b) by 589 days.

(21) Appl. No.: 15/295,029

(22) Filed: Oct. 17, 2016

(65) Prior Publication Data

US 2018/0104128 A1    Apr. 19, 2018

(51) Int. Cl.
| | |
|---|---|
| *A61H 99/00* | (2006.01) |
| *A61F 5/30* | (2006.01) |
| *A61H 1/00* | (2006.01) |
| *A61H 11/00* | (2006.01) |
| *A61F 5/34* | (2006.01) |

(52) U.S. Cl.
CPC ............... *A61H 99/00* (2013.01); *A61F 5/30* (2013.01); *A61H 1/008* (2013.01); *A61H 11/00* (2013.01); *A61F 5/34* (2013.01); *A61H 2011/005* (2013.01); *A61H 2201/0157* (2013.01); *A61H 2201/163* (2013.01); *A61H 2201/165* (2013.01); *A61H 2201/1626* (2013.01); *A61H 2201/1638* (2013.01); *A61H 2201/1642* (2013.01); *A61H 2201/1645* (2013.01)

(58) Field of Classification Search
CPC ............ A61H 39/04; A61H 2201/0157; A61H 2201/0161; A61H 2201/1635; A61H 2201/1652; A61H 2201/1664; A61H 2201/1695; A61H 2201/5053; A61F 5/30–34; A61B 17/12; F16B 2/08; F16B 2/12; F16B 2/18; Y10T 403/32024; Y10T 403/32057; Y10T 403/32073; Y10T 403/32237

USPC ......... 601/134, 33, 42, 56, 58, 62, 143, 144, 601/150; 403/55, 59, 61, 81
See application file for complete search history.

(56) References Cited

U.S. PATENT DOCUMENTS

| | | | | |
|---|---|---|---|---|
| 1,870,052 | A * | 8/1932 | Jones | A61B 17/1327 606/203 |
| 3,219,031 | A * | 11/1965 | Rentsch, Jr. | A61H 31/007 601/41 |
| 6,068,646 | A * | 5/2000 | Lam | A61B 17/1325 606/157 |
| 8,043,237 | B1 * | 10/2011 | Wu | A61H 11/02 601/143 |

(Continued)

*Primary Examiner* — Rachel T Sippel
*Assistant Examiner* — Alexander Morales
(74) *Attorney, Agent, or Firm* — Muncy, Geissler, Olds & Lowe, P.C.

(57) ABSTRACT

A pressurizing device includes a main body and a pressurizing mechanism having a controlling assembly and a pressing assembly arranged on the controlling assembly and movable relative to the main body. The controlling assembly has a base body arranged on the main body and a controlling member having a pivot portion and a driving portion, the pivot portion is pivoted to the base body so that the controlling member is swingable between pressurizing and releasing positions, and the pressing assembly has a controlled portion comovable with the driving portion and a pressurizing portion for pressing an object. When the controlling member swings toward the pressurizing position, the driving portion drives the controlled portion to make the pressurizing portion press the object; when the controlling member swings toward the releasing position, the driving portion drives the controlled portion to depressurize the object.

8 Claims, 5 Drawing Sheets

(56) References Cited

U.S. PATENT DOCUMENTS

| | | | | |
|---|---|---|---|---|
| 8,065,781 | B2* | 11/2011 | Chao | A61B 17/1327 24/265 BC |
| 8,353,927 | B2* | 1/2013 | Lampropoulos | A61B 17/1325 606/204 |
| 8,535,251 | B1* | 9/2013 | Rao | A61H 31/007 601/41 |
| 8,657,850 | B2* | 2/2014 | McNeese | A61B 17/1325 600/490 |
| 9,789,966 | B2* | 10/2017 | De Morais | B64C 1/20 |
| 2012/0324682 | A1* | 12/2012 | Ballentine | F16B 7/1454 24/535 |
| 2014/0031861 | A1* | 1/2014 | Teeslink | A61B 17/0057 606/213 |

* cited by examiner

PRESSURIZING DEVICE

BACKGROUND OF THE INVENTION

Field of the Invention

The present invention relates to a pressurizing device.

Description of the Prior Art

When exercising, one may be injured due to wrong exercising position or overexertion and may suffer from tennis elbow or arthritis. Furthermore, when maintaining a position for too long, one may have health problems like muscle inflammation or joint injury. Therefore, being injured, to protect injured muscles from being injured again due to excessive contractions or to ease pain, one often binds a pressurizing belt on a part injured to exert pressure on a pain spot so as to decrease a tension of the muscle and help the muscle to exert force stably. This type of pressurizing devices are disclosed in TWM404039.

However, in the prior art, a force of the pressure is decided by a tightness of the pressurizing belt binding an object. Since the object is bound tightly circumferentially, when being bound too tightly, people may feel restricted, and the blood circulation is not smooth; but when being bound too loosely, a pressurizing effect is not preferable. In addition, when a user stops using the pressurizing device for a while, s/he needs to adjust the belt repeatedly when wanting to use the pressurizing device again. It is inconvenient and time-consuming.

The present invention has arisen to mitigate and/or obviate the afore-described disadvantages.

SUMMARY OF THE INVENTION

The major object of the present invention is to provide a pressurizing device, which can be quickly switched between a pressurized state and a depressurized state through a controlling member swinging pivotally and can exert an appropriate pressure on a pain spot to ease pain. The pressurizing device has a simple structure, and it is easy, quick and power-saving to operate the pressurizing device.

To achieve the above and other objects, a pressurizing device is provided, including a main body and a pressurizing mechanism. The pressurizing mechanism has a controlling assembly and a pressing assembly, the controlling assembly has a base body and a controlling member, the base body is arranged on the main body, the controlling member has a pivot portion and a driving portion, the pivot portion is pivoted to the base body so that the controlling member is swingable between a pressurizing position and a releasing position, the pressing assembly is arranged on the controlling assembly and movable relative to the main body, and the pressing assembly has a controlled portion which comoves with the driving portion and a pressurizing portion for pressing an object. When the controlling member swings toward the pressurizing position, the driving portion drives the controlled portion to make the pressurizing portion move away from the pivot portion and press the object; when the controlling member swings toward the releasing position, the driving portion drives the controlled portion to make the pressurizing portion to move toward the pivot portion and depressurize the object.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Please refer to FIGS. 1 to 7 for a preferred embodiment of the present invention. A pressurizing device includes a main body 1 and a pressurizing mechanism 2.

Figure 1:
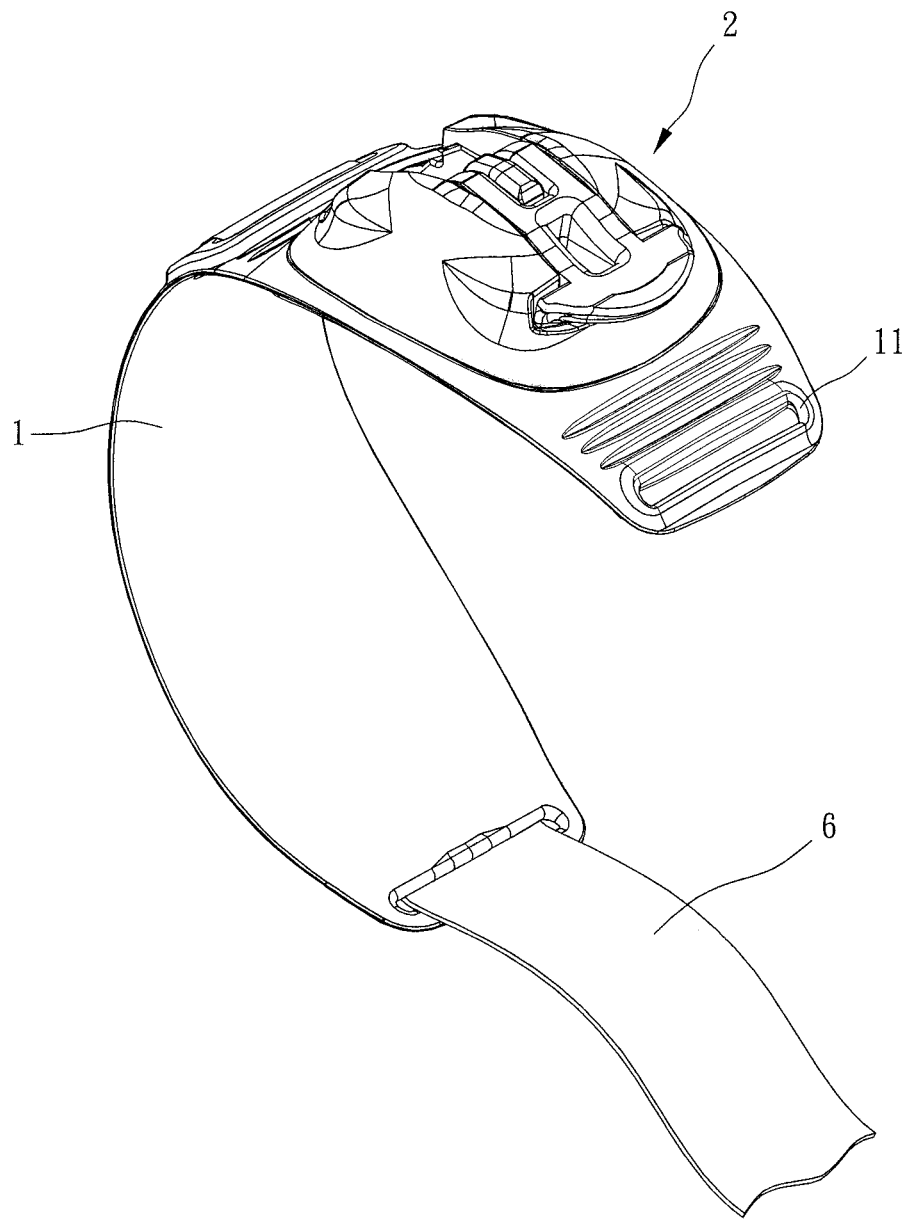
FIG. 1 is a stereogram of a preferred embodiment of the present invention.
Figure 2:
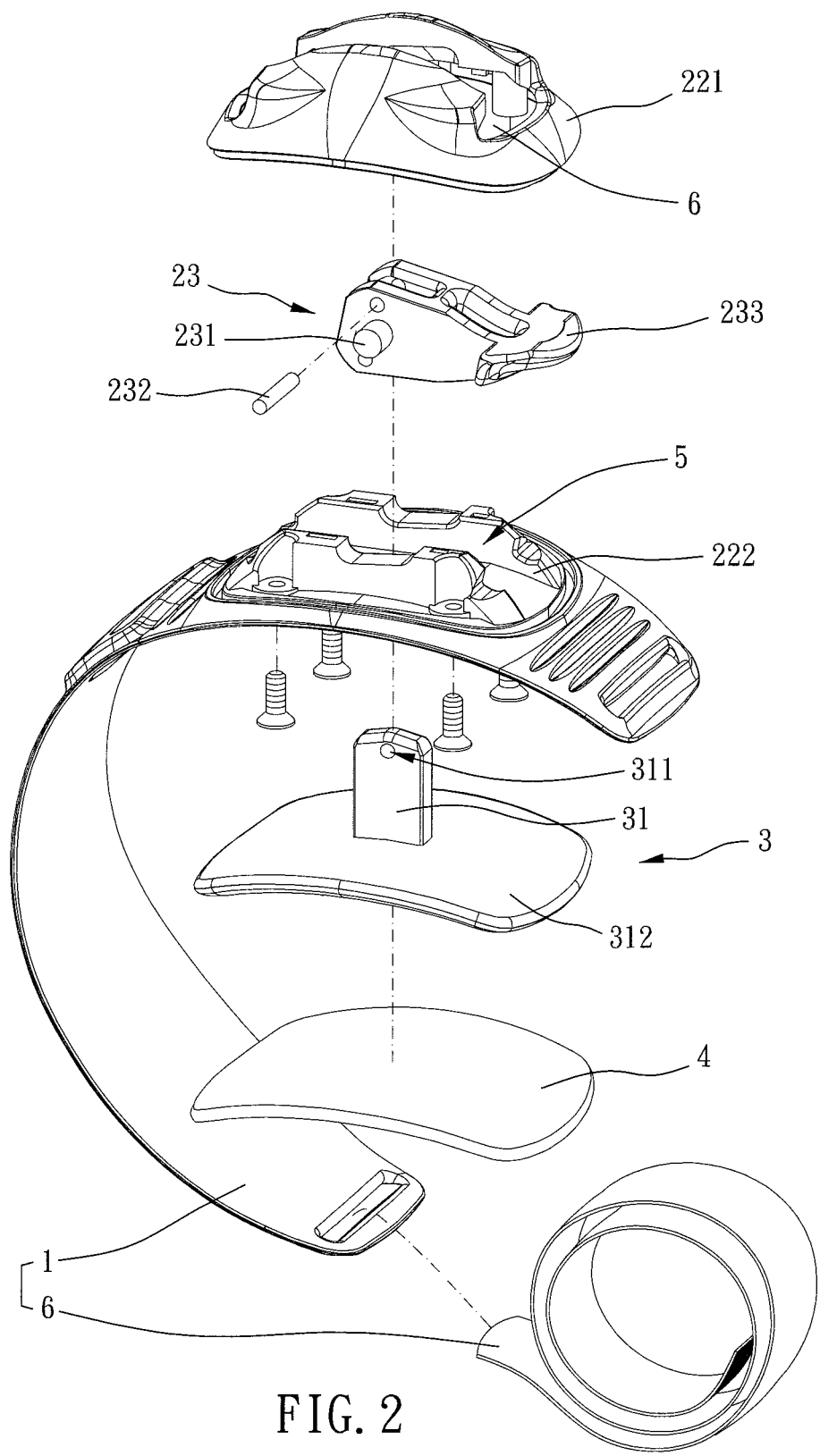
FIG. 2 is a breakdown view of FIG. 1.
Figure 3:
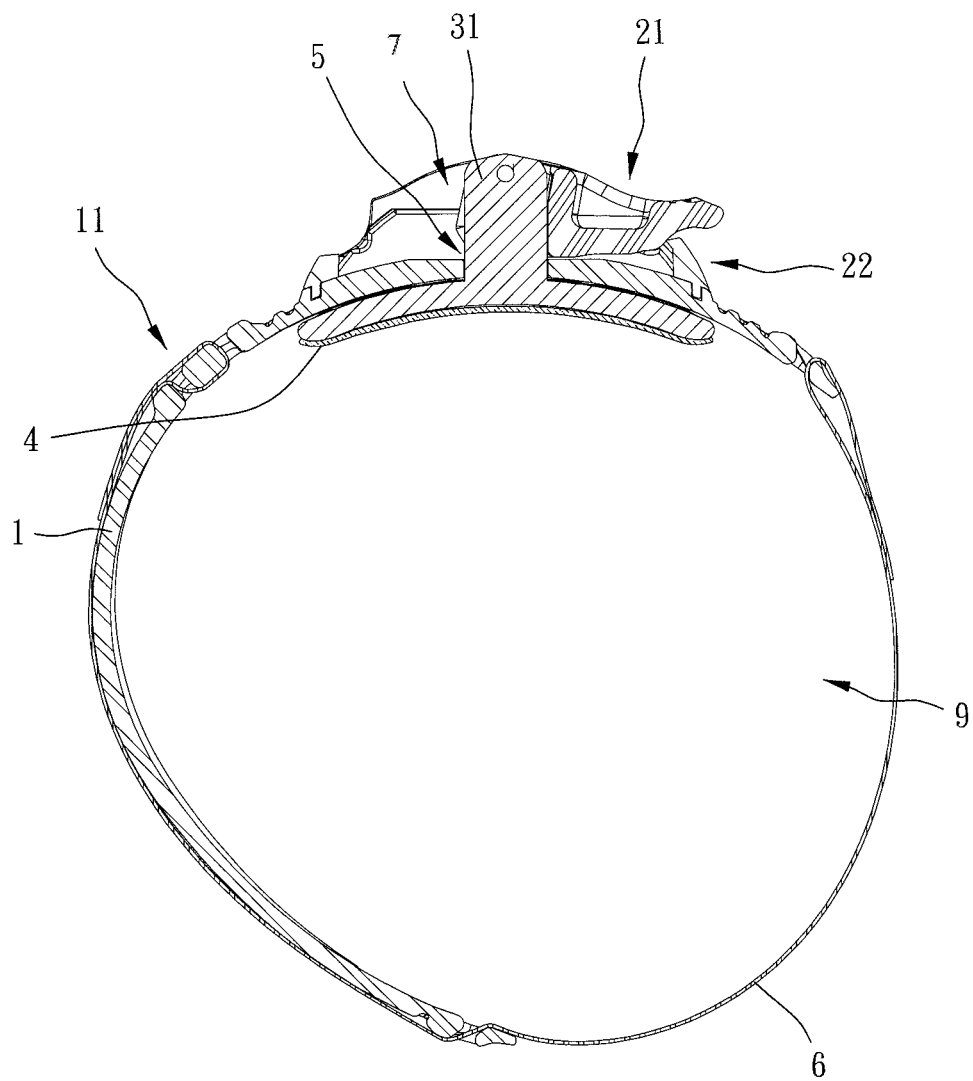
FIG. 3 is a cross-sectional view of FIG. 1.
Figure 4:
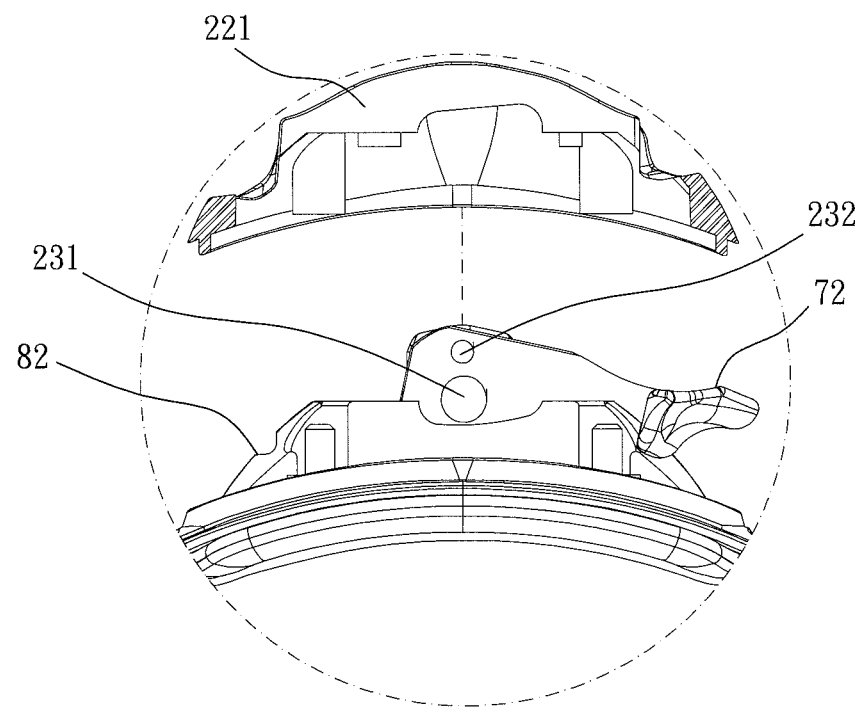
FIG. 4 is a partially breakdown view of a base body of the present invention.
Figure 5:
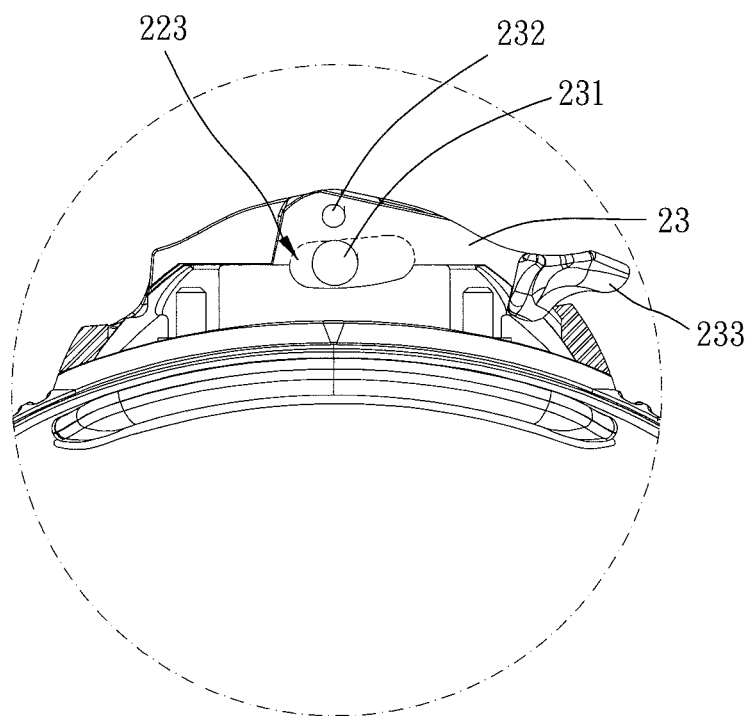
FIGS. 5 to 7 are drawings showing operation of the present invention.
Figure 7:
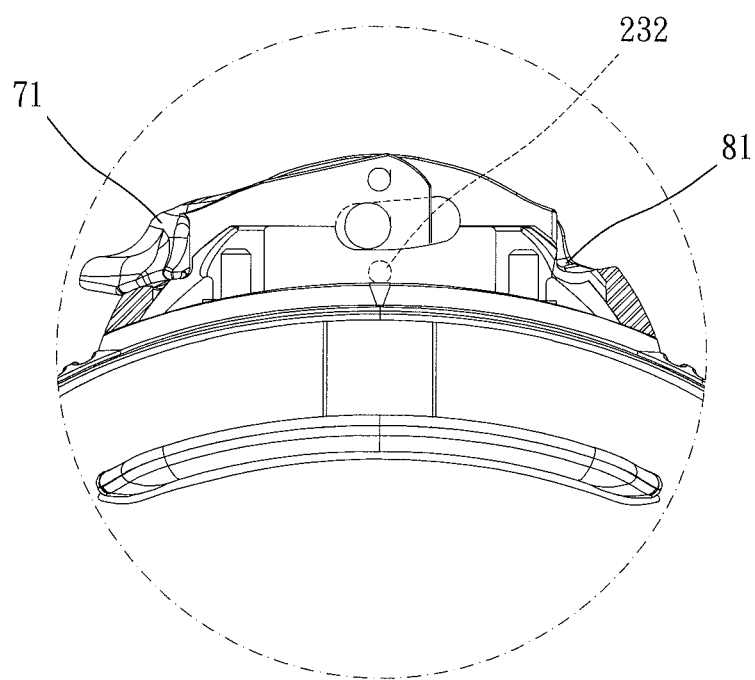

The pressurizing mechanism 2 has a controlling assembly 21 and a pressing assembly 3, the controlling assembly 21 has a base body 22 and a controlling member 23, the base body 22 is arranged on the main body 1, the controlling member 23 has a pivot portion 231 and a driving portion 232, the pivot portion 231 is pivoted to the base body 22 so that the controlling member 23 is swingable between a pressurizing position and a releasing position, the pressing assembly 3 is arranged on the controlling assembly 21 and movable relative to the main body 1, and the pressing assembly 3 has a controlled portion 311 which comoves with the driving portion 232 and a pressurizing portion 312 for pressing an object (for example, an elbow, not shown). When the controlling member 23 swings toward the pressurizing position, the driving portion 232 drives the controlled portion 311 to make the pressurizing portion 312 move away from the pivot portion 231 and press the object (as shown in FIG. 7); when the controlling member 23 swings toward the releasing position, the driving portion 232 drives the controlled portion 311 to make the pressurizing portion 312 to move toward the pivot portion 231 and depressurize the object (as shown in FIG. 5).

When the pressurizing device is used on a human body, the pressurizing portion 312 can exert pressure on a pain spot to stabilize a muscle to exert force, ease pain, and prevent the muscle from excessive contractions. It is understandable that the pressing assembly 3 further has a connecting member 31, the connecting member 31 is connected to the controlling member 23 and the pressurizing portion 312, and the connecting member 31 has the controlled portion 311. Preferably, the pressing assembly 3 further has a cushion member 4, the cushion member 4 covers the pressurizing portion 312, and the pressurizing portion 312 is located between the cushion member 4 and the base body 22 so as to prevent the pressurizing portion 312 from getting dirty or from being impacted directly. Preferably, the cushion member 4 is made of a flexible material, such as foam or a gel cushion piece; therefore, when a user wears the pressurizing device, the cushion member 4 makes the user feel more comfortable; and when the pressurizing device is used on an item, the cushion member 4 can prevent a surface of the item from being damaged.

Figure 6:
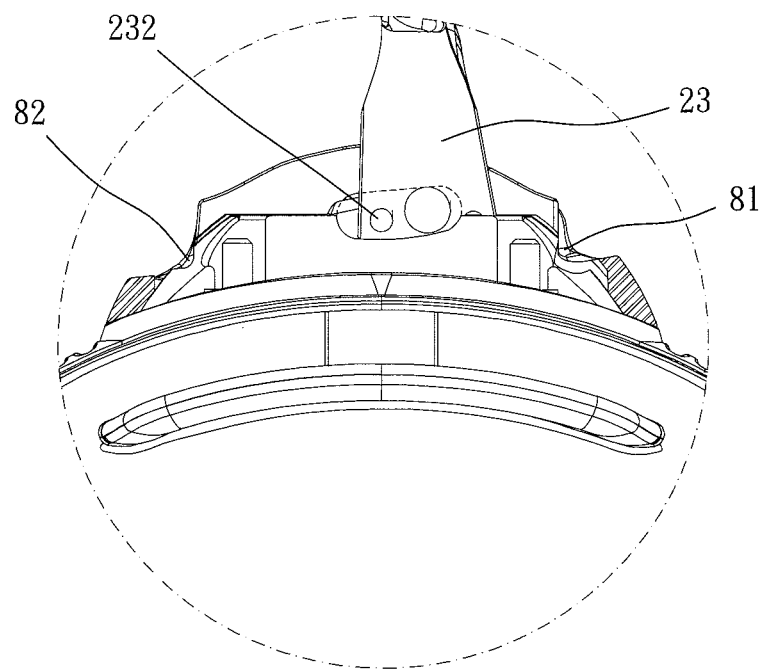

In addition, the main body 1 is located between the base body 22 and the pressurizing portion 312, the main body 1 has a through hole 5, the base body 22 has a through hole 7 which corresponds to the through hole 5 of the main body 1, and the connecting member 31 is disposed through the through holes 5, 7 to be connected to the controlling member 23. Specifically, opening directions of the through holes 5, 7 are defined as a first direction, and at least one of walls of the through holes 5, 7 restricts the connecting member 31 to move along the first direction so as to prevent the connecting member 31 from shaking and from colliding with the base body 22 or the main body 1 and being damaged or broken. In this embodiment, the connecting member 31 is pivoted to the controlling member 23 and non-coaxially arranged to the pivot portion 231, the base body 22 further has a sliding groove 223, an extension direction of the sliding groove 223 is lateral to the first direction, and when the controlling member 23 swings between the pressurizing position and the releasing position, the pivot portion 231 slidably moves within the sliding groove 223 according to a swinging angle of the controlling member 23 (as shown in FIGS. 5 to 7).

It is to be noted that the controlling member 23 pivots in a leverage way, so the user can quickly switch the controlling member 23 to be in the pressurizing position or the releasing position. A switching process is time-saving, easy and energy-saving. In addition, when a time to be pressurized is reached, the user does not need to disassemble the whole pressurizing device from the object, the user only needs to toggle the controlling member 23 to the releasing position. Preferably, the controlling member 23 further extends to form a toggle portion 233 for being operated from outside so that the user can toggle and control the controlling member 23 with fingers. More preferably, the base body 22 further has a first positioning portion 81 and a second positioning portion 82, and the controlling member 23 further has a first engaging portion 71 and a second engaging portion 72; when the controlling member 23 is in the releasing position, the first engaging portion 71 and the first positioning portion 81 are engaged and positioned with each other, and when the controlling 23 is in the pressurizing position, the second engaging portion 72 and the second positioning portion 82 are engaged and positioned with each other.

In this embodiment, the base body 22 is divided into a cover body 221 and a seat body 222, the seat body 222 is arranged on the main body 1, the cover body 221 covers the seat body 222, and the seat body 222 has the first and second positioning portions 81, 82. The first and second positioning portions 81, 82 are respectively engaged with the first and second engaging portions 71, 72 to be positioned with each other. It is to be noted that in other embodiments, the seat body may integrally extend from the main body.

In addition, the pressurizing device further includes a binding member 6, the main body 1 further has at least one connecting portion 11, the binding member 6 is connected to the at least one connecting portion 11, the binding member 6 optionally defines an arranging space 9 with the main body 1, the arranging space 9 is for the object to be arranged therethrough, and the binding member 6 can not only fix the main body 1 on the object but also bind/pressurize the object. It is understandable that a pressurizing force of each user varies, a dimension of the arranging space 9 can be changed by adjusting a length of the blinding member 6 so as to change a tightness of the binding member 6 binding the object and to further adjust the pressurizing force of the pressurizing portion 312 exerted on the object.

Preferably, the main body 1 is made of a flexible material, for example but not limited to rubber or soft plastic, and the main body 1 is deformable as the binding member 6 being pulled tightly so as to contact the object. In other embodiments, the at least one connecting portion 11 is a through slot, and the binding member 6 is a sticky buckle belt with a length which is adjustable. Of course, in other embodiments, the main body may directly extends to form the binding member.

Given the above, the controlling member of the pressurizing device pivots in the leverage way, so the user can quickly switch the controlling member to be in the pressurizing position or the releasing position. The user can quickly pressurize the object through the pressurizing portion. It is easy, convenient and energy-saving to operate the pressurizing device. In addition, the base body has the positioning portions to keep the controlling member in the pressurizing position or the releasing position. Furthermore, a force of the pressurizing portion can be adjusted via the binding member.

While we have shown and described various embodiments in accordance with the present invention, it should be clear to those skilled in the art that further embodiments may be made without departing from the scope of the present invention.

What is claimed is:
1. A pressurizing device, including:
a main body;
a pressurizing mechanism, having a controlling assembly and a pressing assembly, the controlling assembly having a base body and a controlling member, the base body being arranged on the main body, the controlling member having a pivot portion and a driving portion, the pivot portion being pivoted to the base body so that the controlling member is swingable between a pressurizing position and a releasing position, the pressing assembly being arranged on the controlling assembly and movable relative to the main body, the pressing assembly having
a controlled portion which comoves with the driving portion and a pressurizing portion for pressing an object;
wherein when the controlling member swings toward the pressurizing position, the driving portion drives the controlled portion to make the pressurizing portion move away from the pivot portion and press the object; when the controlling member swings toward the releasing position, the driving portion drives the controlled portion to make the pressurizing portion to move toward the pivot portion and depressurize the object;
wherein the base body further has a first positioning portion and a second positioning portion, the controlling member further has a first engaging portion and a second engaging portion; the base body further has a sliding groove, and the pivot portion is limitedly movable only within the sliding groove; when the controlling member is in the releasing position, the first engaging portion and the first positioning portion are engaged and positioned with each other; and when the controlling member is in the pressurizing position, the second engaging portion and the second positioning portion are engaged and positioned with each other;
wherein the controlling member and the driving portion are simultaneously swingable about the pivot portion;

wherein when the controlling member is in the releasing position, the pivot portion is moved to be located between the driving portion and the pressurizing portion, when the controlling member is in the pressurizing position, the driving portion is moved to be located between the pivot portion and the pressurizing portion and under the sliding groove;

wherein the first positioning portion and the second positioning portion are located at opposite sides of the pivot portion, the driving portion and the sliding groove;

wherein the sliding groove linearly extends slantly upward in a direction from the second positioning portion toward the first positioning portion.

2. The pressurizing device of claim 1, further including a binding member, the main body further having at least one connecting portion, the binding member being connected to the at least one connecting portion, the binding member defining an arranging space with the main body, the arranging space for the object to be arranged therethrough.

3. The pressurizing device of claim 1, wherein the pressing assembly further has a cushion member, the cushion member covers the pressurizing portion, and the pressurizing portion is located between the cushion member and the base body.

4. The pressurizing device of claim 1, wherein the pressing assembly further has a connecting member, the connecting member is connected to the controlling member and the pressurizing portion, and the connecting member has the controlled portion.

5. The pressurizing device of claim 4, wherein the main body is located between the base body and the pressurizing portion, the main body has a through hole, the base body has a through hole which corresponds to the through hole of the main body, and the connecting member is disposed through the through holes to be connected to the controlling member.

6. The pressurizing device of claim 5, wherein at least one wall of the through holes restricts the connecting member to move along a first direction passing through the through holes.

7. The pressurizing device of claim 6, wherein the connecting member is pivoted to the controlling member and non-coaxially arranged to the pivot portion, and an extension direction of the sliding groove is lateral to the first direction.

8. The pressurizing device of claim 7, wherein the controlling member further extends to form a toggle portion for being operated from outside; the base body is divided into a cover body and a seat body, the seat body is arranged on the main body, the cover body covers the seat body, and the seat body has the first and second positioning portions; the first and second positioning portions are respectively engaged with the first and second engaging portions to be positioned with each other; the pressurizing device further includes a binding member, the main body further has at least one connecting portion, the binding member is connected to the at least one connecting portion, the binding member defines an arranging space with the main body, and the arranging space is for the object to be arranged therethrough; the at least one connecting portion is a through slot, the binding member is a sticky buckle belt with a length which is adjustable; the pressing assembly further has a cushion member, the cushion member covers the pressurizing portion, and the pressurizing portion is located on the cushion member and base body; the main body is made of a flexible material; the cushion member is flexible.

* * * * *